(12) United States Patent
Toda

(10) Patent No.: US 10,053,058 B2
(45) Date of Patent: *Aug. 21, 2018

(54) SEMICONDUCTOR DEVICE, WIPER SYSTEM, AND MOVING BODY CONTROL METHOD

(71) Applicant: LAPIS SEMICONDUCTOR CO., LTD., Kanagawa (JP)

(72) Inventor: Kentaro Toda, Kanagawa (JP)

(73) Assignee: LAPIS SEMICONDUCTOR CO., LTD., Yokohama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/804,313

(22) Filed: Nov. 6, 2017

(65) Prior Publication Data

US 2018/0056944 A1    Mar. 1, 2018

Related U.S. Application Data

(63) Continuation of application No. 15/018,881, filed on Feb. 9, 2016, now Pat. No. 9,827,951.

(30) Foreign Application Priority Data

Feb. 26, 2015    (JP) .................................. 2015-037449

(51) Int. Cl.
   *B60S 1/08*       (2006.01)
   *G05B 19/00*      (2006.01)
   (Continued)

(52) U.S. Cl.
   CPC ............ *B60S 1/0807* (2013.01); *G01N 29/14* (2013.01); *G05B 19/00* (2013.01); *B60S 1/0818* (2013.01); *B60S 1/0859* (2013.01); *B60S 1/3411* (2013.01)

(58) Field of Classification Search
   CPC ........ B60S 1/04; B60S 1/0444; B60S 1/0452; B60S 1/08; B60S 1/0803; B60S 1/0807;
   (Continued)

(56) References Cited

U.S. PATENT DOCUMENTS 3,110,056 A    11/1963   Oishei et al.
3,292,200 A    12/1966   Scinta
(Continued)

FOREIGN PATENT DOCUMENTS

DE    3736049 A1 *   5/1989   ............ B60S 1/0818
DE   19823431 A1 *  12/1999   ................ B60S 1/08
(Continued)

*Primary Examiner* — Angelina Shudy
(74) *Attorney, Agent, or Firm* — Volentine, Whitt & Francos, PLLC

(57) ABSTRACT

A semiconductor device including an abnormality detection section that detects an abnormality occurring in a moving body that moves along a specific path on a surface of a specific object; a position detection section that detects a position of the moving body as an abnormality occurrence position, in a case in which the abnormality detection section has detected an abnormality, and that stores abnormality occurrence position information expressing the abnormality occurrence position in a storage section; and a moving body controller that controls an adjusting section to adjust at least one of a force with which the moving body presses against the specific object, or a position of the moving body in a direction intersecting the surface of the specific object, based on a detection result detected by the abnormality detection section and the abnormality occurrence position information.

8 Claims, 6 Drawing Sheets

(51) Int. Cl.
*G01N 29/14* (2006.01)
*B60S 1/34* (2006.01)

(58) Field of Classification Search
CPC .... B60S 1/0818; B60S 1/0859; B60S 1/3411; G01N 29/04; G01N 29/14; G01N 2291/023; G05B 19/00
USPC ............... 701/36, 49; 15/250, 202, 250.203; 318/443
See application file for complete search history.

(56) References Cited

U.S. PATENT DOCUMENTS

| | | | | |
|---|---|---|---|---|
| 4,431,954 A | * | 2/1984 | Carpenter | B60S 1/0814 15/250.13 |
| 4,542,325 A | | 9/1985 | Kobayashi et al. | |
| 4,588,935 A | | 5/1986 | Kaneiwa et al. | |
| 4,689,535 A | | 8/1987 | Tsunoda et al. | |
| 4,718,139 A | * | 1/1988 | Okuda | B60S 1/3411 134/15 |
| 4,728,870 A | | 3/1988 | Hirano et al. | |
| 4,777,695 A | * | 10/1988 | Okuda | B60S 1/3411 15/250.203 |
| 4,797,601 A | * | 1/1989 | Ditzer | B60S 1/3411 15/250.01 |
| 4,918,272 A | | 4/1990 | Nishikawa | |
| 4,993,102 A | * | 2/1991 | Honda | B60S 1/245 15/250.13 |
| 5,030,899 A | | 7/1991 | Nishibe et al. | |
| 5,046,215 A | * | 9/1991 | Kobayashi | B60S 1/3411 15/250.203 |
| 5,049,794 A | | 9/1991 | Okada et al. | |
| 5,056,182 A | * | 10/1991 | Fukumoto | B60S 1/3411 15/250.202 |
| 5,062,175 A | * | 11/1991 | Buchanan | B60S 1/3411 15/250.203 |
| 5,070,571 A | | 12/1991 | Arai | |
| 5,129,123 A | * | 7/1992 | Shirato | B60S 1/3411 15/250.203 |
| 5,161,280 A | * | 11/1992 | Sumiya | B60S 1/3411 15/250.202 |
| 5,421,055 A | * | 6/1995 | Harmon | B60S 1/3411 15/250.202 |
| 5,430,907 A | * | 7/1995 | Jutras | B60S 1/34 15/250.21 |
| 5,481,778 A | * | 1/1996 | Battlogg | B60S 1/3406 15/250.16 |
| 5,504,406 A | * | 4/1996 | Shultz | B60S 1/0814 15/250.203 |
| 5,577,292 A | * | 11/1996 | Blachetta | B60S 1/3411 15/250.202 |
| 5,771,527 A | * | 6/1998 | Blachetta | B60S 1/34 15/250.202 |
| 5,822,827 A | * | 10/1998 | Dimatteo | B60S 1/0896 15/250.203 |
| 5,857,236 A | * | 1/1999 | Sakurai | B60S 1/3413 15/250.202 |
| 6,107,766 A | | 8/2000 | Amagasa | |
| 6,129,093 A | | 10/2000 | Kelly | |
| 6,249,098 B1 | * | 6/2001 | Miyazaki | B60S 1/08 15/250.12 |
| 6,354,578 B1 | | 3/2002 | Nakatsukasa et al. | |
| 6,400,110 B1 | * | 6/2002 | Yabe | B60S 1/08 318/443 |
| 9,048,763 B2 | * | 6/2015 | Bonnefous | H02P 7/00 |
| 9,061,657 B2 | | 6/2015 | Natsume | |
| 9,395,337 B2 | * | 7/2016 | Newman | F03D 17/00 |
| 9,527,480 B2 | * | 12/2016 | Braun | B60S 1/0814 |
| 9,827,951 B2 | * | 11/2017 | Toda | B60S 1/0807 |
| 2002/0003411 A1 | | 1/2002 | Okai et al. | |
| 2004/0168278 A1 | * | 9/2004 | Lebel | B60S 1/3411 15/250.202 |
| 2005/0138751 A1 | | 6/2005 | Bauer et al. | |
| 2006/0113942 A1 | | 6/2006 | Amagasa | |
| 2008/0209663 A1 | * | 9/2008 | Merkel | B60S 1/345 15/250.351 |
| 2009/0108788 A1 | | 4/2009 | Willey | |
| 2009/0119865 A1 | | 5/2009 | Amagasa et al. | |
| 2009/0125183 A1 | | 5/2009 | Amagasa et al. | |
| 2012/0297567 A1 | | 11/2012 | Hyer | |
| 2013/0162180 A1 | | 3/2013 | Zimmer et al. | |
| 2013/0312210 A1 | * | 11/2013 | Kim | B60S 1/0491 15/250.451 |
| 2014/0013535 A1 | | 1/2014 | Natsume | |
| 2014/0366304 A1 | * | 12/2014 | Wilms | B60S 1/0859 15/250.32 |
| 2015/0105974 A1 | * | 4/2015 | Kleve | B60W 10/00 701/36 |
| 2016/0221539 A1 | * | 8/2016 | Hackl | B60S 1/3801 |
| 2016/0250997 A1 | * | 9/2016 | Toda | B60S 1/0807 701/49 |
| 2016/0276899 A1 | | 9/2016 | Ikeda | |

FOREIGN PATENT DOCUMENTS

| | | | | |
|---|---|---|---|---|
| FR | 2739075 A1 | * | 3/1997 | ............ B60S 1/3411 |
| JP | A 1988159161 | | 7/1988 | |
| JP | 04126645 A | * | 4/1992 | ............ B01J 23/44 |
| JP | A 1996290756 | | 4/1995 | |
| JP | H08290756 A | | 11/1996 | |
| JP | A 1998194090 | | 7/1998 | |
| JP | 2819515 B2 | | 10/1998 | |
| JP | 20090033941 A | | 4/2009 | |
| JP | 2015189283 A | | 11/2015 | |
| KR | 20110076273 A | * | 7/2011 | ............ B60S 1/347 |

\* cited by examiner

SEMICONDUCTOR DEVICE, WIPER SYSTEM, AND MOVING BODY CONTROL METHOD

CROSS-REFERENCE TO RELATED APPLICATION

This application is a continuation application of application Ser. No. 15/018,881, filed on Feb. 9, 2016, which claims priority under 35 USC 119 from Japanese Patent Application No. 2015-037449, filed on Feb. 26, 2015, the disclosure of which is incorporated by reference herein.

BACKGROUND

Technical Field

The present disclosure relates to a semiconductor device, a wiper system, and a moving body control method.

Related Art

Conventionally, a technology in which an abnormality occurring in a moving body moving along a specific path over a surface of a specific object is detected, and the abnormality is suppressed, is known.

For example, an abnormality such as "chattering" may occur, in which wipers that move to-and-fro across the surface of window glass of a vehicle vibrate so as to jump up from the window glass. Technology to suppress such chattering is known. For example, Japanese Patent Application Laid-Open (JP-A) No. H08-290756 discloses a technology that suppress chattering by increasing the movement speed of a wiper, or increasing the pressing force of a wiper blade. As another example, JP-A No. H10-194090 discloses a technology that suppress chattering by generating a signal of the reverse-phase to chattering vibration, combining the generated signal with a drive signal for when chattering is not occurring, and driving the wiper by employing the combined drive signal.

However, in the technology described in JP-A No. H08-290756 and JP-A No. H10-194090, chattering may not be sufficiently suppressed always, and in some cases, chattering may not be appropriately controlled.

Accordingly, technology to appropriately suppress an abnormality occurring during movement of a moving body is desired.

SUMMARY

The present disclosure provides a semiconductor device, a wiper system, and a moving body control method that may appropriately suppress an abnormality occurring during movement of a moving body.

A first aspect of the present disclosure is a semiconductor device including: an abnormality detection section that detects an abnormality occurring in a moving body that moves along a specific path on a surface of a specific object; a position detection section that detects a position of the moving body as an abnormality occurrence position, in a case in which the abnormality detection section has detected an abnormality, and that stores abnormality occurrence position information expressing the abnormality occurrence position in a storage section; and a moving body controller that controls an adjusting section to adjust at least one of a force with which the moving body presses against the specific object, or a position of the moving body in a direction intersecting the surface of the specific object, based on a detection result detected by the abnormality detection section and the abnormality occurrence position information.

A second aspect of the present disclosure, in the semiconductor of the first aspect, the specific object may be a vehicle window; the moving body may be a wiper; and the abnormality may be chattering.

A third aspect of the present disclosure is a moving body control method including processing of: detecting, by an abnormality detection section, an abnormality occurring in a moving body that moves along a specific path on a surface of a specific object; detecting, by a position detection section, a position of the moving body as an abnormality occurrence position, in a case in which the abnormality detection section has detected an abnormality, and storing, by a position detection section, abnormality occurrence position information expressing the abnormality occurrence position in a storage section; and controlling, by a moving body controller, an adjusting section to adjust at least one of a force with which the moving body is pressed against the specific object, or a position of the moving body in a direction intersecting the surface of the specific object, based on a detection result detected by the abnormality detection section and the abnormality occurrence position information.

According to the above aspects, the present disclosure may suppress an abnormality occurring during movement of a moving body.

BRIEF DESCRIPTION OF THE DRAWINGS

Exemplary embodiments will be described in detail based on the following figures, wherein.

DETAILED DESCRIPTION

Detailed explanation follows regarding respective exemplary embodiments, with reference to the drawings.

First Exemplary Embodiment

Figure 1:
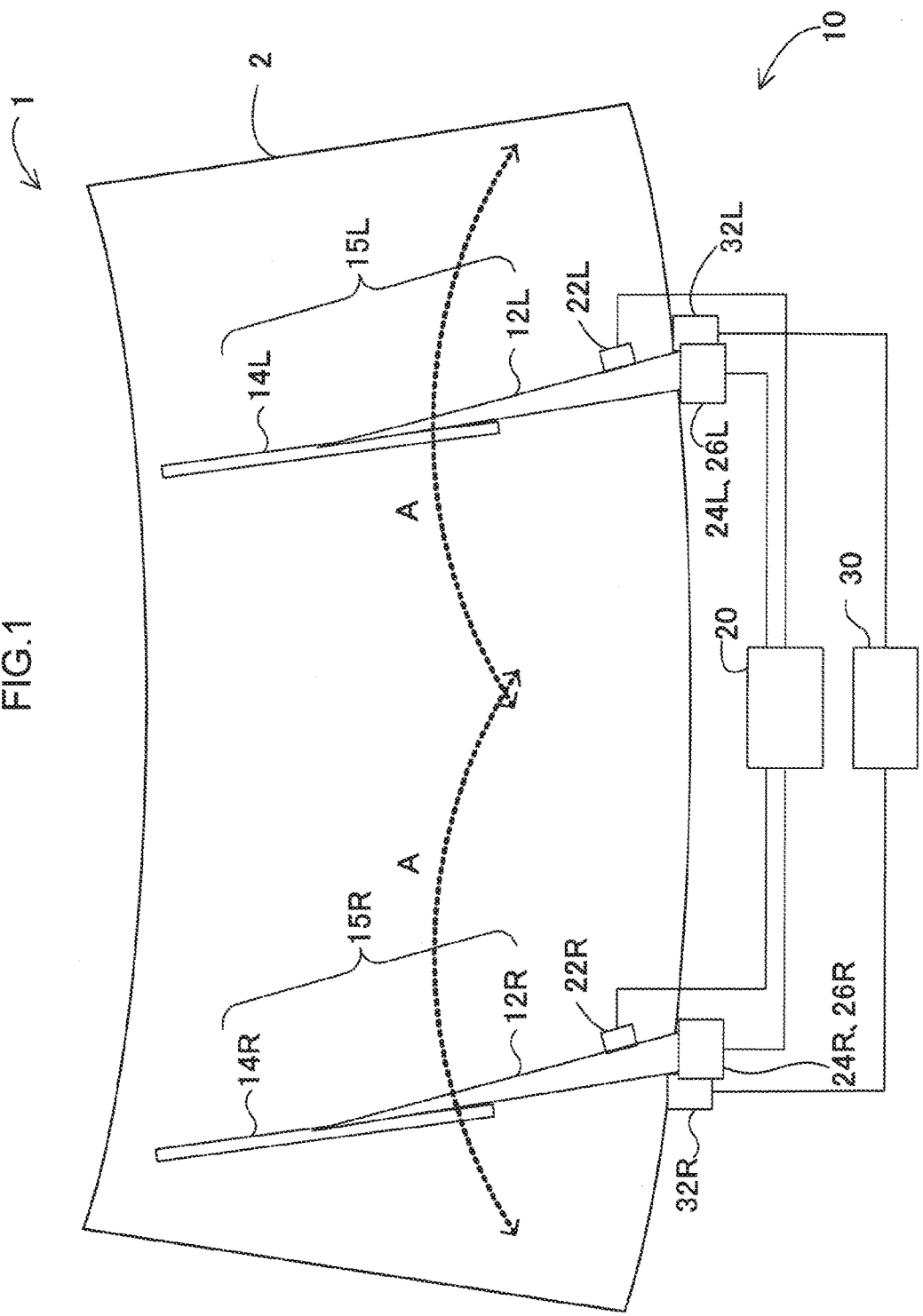
FIG. 1 is a configuration diagram schematically illustrating a wiper system of a first exemplary embodiment.
Figure 2:
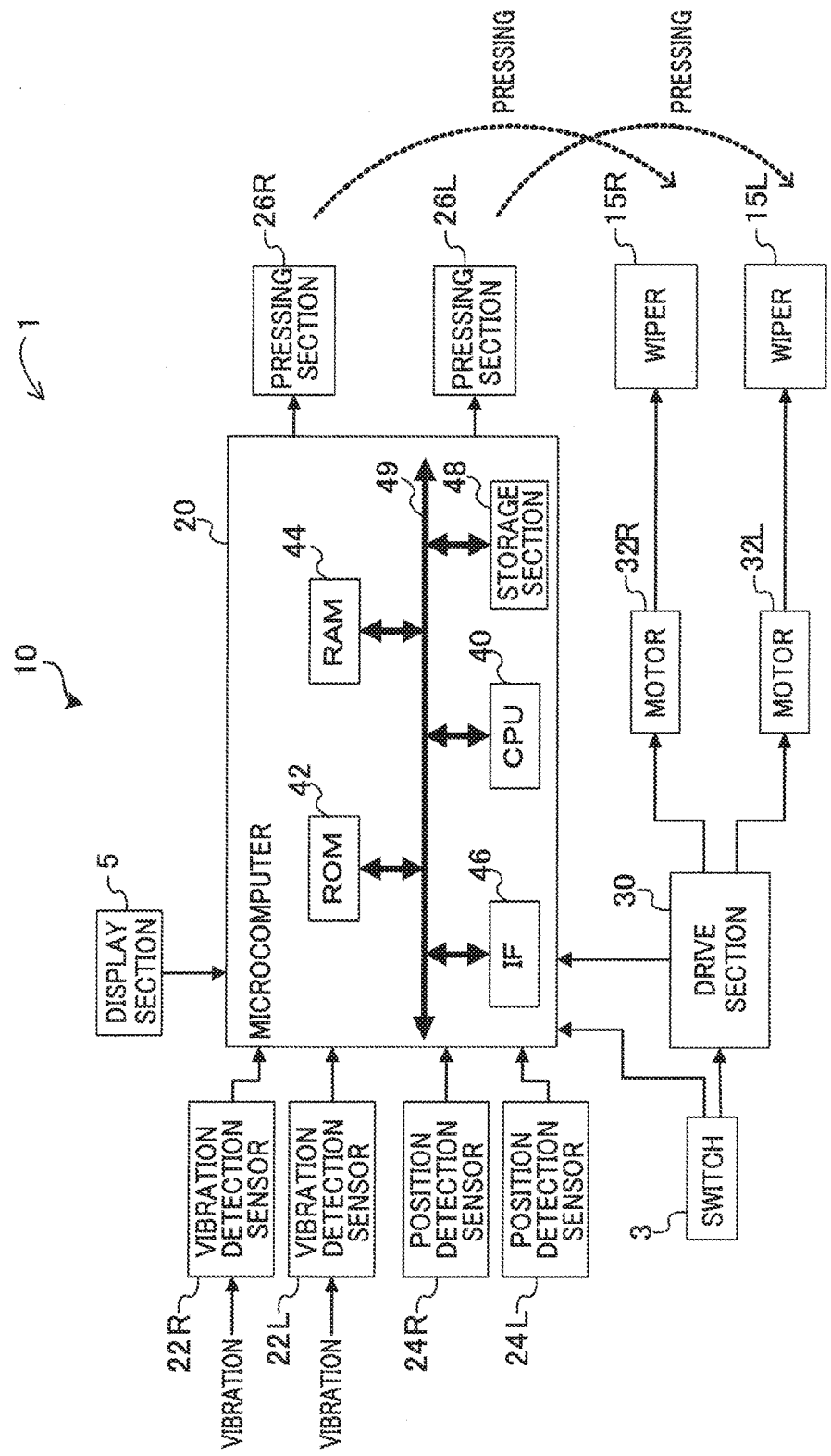
FIG. 2 is a block diagram illustrating a wiper system of the first exemplary embodiment.

First, explanation follows regarding configuration of a wiper system of the present exemplary embodiment. FIG. 1 is a configuration diagram schematically illustrating a wiper system 10 of the present exemplary embodiment. FIG. 2 is a block diagram illustrating the wiper system 10 of the present exemplary embodiment.

As illustrated in FIG. 1, the wiper system 10 of the present exemplary embodiment has a function of wiping the surface of a window glass 2 (which is an example of a specific object of the present disclosure) of a vehicle 1, using a pair of left and right wipers 15R, 15L that move to-and-fro across the surface of the window glass 2 of a vehicle 1 in the directions indicated by arrows A.

Generally, as the wipers 15R, 15L move to-and-fro, in some cases, what is known as chattering (namely, irregular vibrations) that cause the wipers 15R, 15L to jump in a direction intersecting with the surface of the window glass 2, occurs due to differences in the amount of water droplets on the surface of the window glass 2, dust and oily substances adhering to the surface of the window glass 2, deterioration of wiper blades 14, or the like.

Accordingly, the wiper system 10 of the present exemplary embodiment has a function of suppressing chattering of the wipers 15R, 15L from occurring.

As illustrated in FIG. 1, the wiper system 10 of the present exemplary embodiment includes the wipers 15R, 15L, a microcomputer 20, vibration detection sensors 22R, 22L, position detection sensors 24R, 24L, pressing sections 26L, 26R, a drive section 30, and motors 32L, 32R. Note that, hereinafter, the wipers 15R, 15L, the vibration detection sensors 22R, 22L, the position detection sensors 24R, 24L, the pressing sections 26L, 26R, and the motors 32L, 32R, may be collectively referred to as the wipers 15, the vibration detection sensors 22, the position detection sensors 24, the pressing sections 26, and the motors 32. Further, the respective letters R and L may be appended after the reference numerals when described individually.

The wipers 15 are an example of a moving body. The wiper 15R is provided at a right side of a lower portion of the window glass 2 of the vehicle 1. The wiper 15R includes a wiper arm 12R and a wiper blade 14R. The wiper blade 14R wipes water droplets and the like that have adhered to the window glass 2. The wiper arm 12R supports the wiper blade 14R. The wiper 15L is provided at a left side of the lower portion of the window glass 2 of the vehicle 1. The wiper 15L includes a wiper arm 12L and a wiper blade 14L. The wiper blade 14L wipes water droplets and the like that have adhered to the window glass 2. The wiper arm 12L supports the wiper blade 14L.

In the following, the wiper arms 12R, 12L and the wiper blades 14R, 14L, may be collectively referred to as the wiper arms 12 and the wiper blades 14, respectively. The respective letters R and L may be appended after the reference numerals when they are described individually.

Pressing springs (not illustrated in the drawings) are provided to the wiper arms 12 of the wipers 15, and the wiper blades 14 are pressed against the window glass 2 by the pressing springs.

The wiper arms 12 of the wipers 15 are coupled to the respective motors 32 through speed reduction mechanisms or the like (not illustrated in the drawings). The motors 32 are connected to the drive section 30. The drive section 30 generates drive signals to drive the wipers 15, and outputting the drive signals to the motors 32. The vehicle 1 is provided with a switch 3 for a user to give instructions relating to drive of the wipers 15, such as the movement speed of the wipers 15.

In a case in which the drive section 30 is input with a signal from the switch 3, a drive signal corresponding to the instructed movement speed or the like, is generated based on this signal and is output to the motors 32. The motors 32 drives the wipers 15 based on the drive signals. The drive section 30 may be configured by a microcomputer, similarly to the microcomputer 20, described later, or may be configured by an analogue circuit.

As illustrated in FIG. 1, in the wiper system 10 of the present exemplary embodiment, the vibration detection sensors 22 are provided to the wiper arms 12 of the wipers 15. The vibration detection sensors 22 are an example of an abnormality detection sensor, and have a function of detecting vibration of the wipers 15. In the present exemplary embodiment, acceleration sensors are employed as specific examples of the vibration detection sensors 22. The vibration detection sensors 22, these being acceleration sensors, detects vibration of the wipers 15, and outputs acceleration values to the microcomputer 20 according to the detected vibration. The microcomputer 20 determines whether or not chattering of the wipers 15 has occurred based on the acceleration values (signals expressing the acceleration values) input from the vibration detection sensors 22. As a specific example, in the present exemplary embodiment, the microcomputer 20 is set with a threshold value, determines that the wiper 15 is vibrating and the chattering is occurring in a case in which the acceleration values input from the vibration detection sensor 22 exceed the threshold value, and determines that chattering is not occurring when the threshold value is not exceeded. The threshold value may be set based on an acceleration value at which chattering does not occur, or may be set in consideration of a permissible chattering range. In the present exemplary embodiment, the microcomputer 20 determines whether or not chattering is occurring for the individual wipers 15R, 15L based on the acceleration values input from the respective vibration detection sensors 22R, 22L.

The vibration detection sensors 22 are not limited to acceleration sensors, as long as they are capable of detecting vibration of the wipers 15 (wiper arms 12). For example, the vibration detection sensors 22 may be strainmeters. In a case in which strainmeters are employed, strain arising in the wipers 15 (wiper arms 12) may be detected, and signals expressing the detection results may be output to the microcomputer 20.

In the wiper system 10 of the present exemplary embodiment, the wipers 15 are provided with the position detection sensors 24. The position detection sensors 24 detects the position on the path (referred to simply as "position" hereafter) of the wipers 15. In the present exemplary embodiment, rotation sensors are employed as a specific example of the position detection sensors 24. The position detection sensors 24 detects the rotation angles of the respective motors 32, and outputs detection results (signals expressing the detection results) to the microcomputer 20. The microcomputer 20 detects a position where chattering of the wiper 15 has occurred based on the detection result input from the respective position detection sensor 24. Note that the microcomputer 20 of the present exemplary embodiment detects the positions of the wipers 15 for the individual wipers 15R, 15L, based on the detection results input from the respective position detection sensors 24R, 24L.

Note that the position detection sensors 24 are not limited to rotation sensors, as long as they are capable of detecting the positions of the wipers 15 (wiper arms 12).

The microcomputer 20 of the present exemplary embodiment suppresses chattering of the wipers 15 from occurring. Moreover, under specific conditions (described in detail later), in a case in which chattering of the wipers 15 has occurred, the microcomputer 20 of the present exemplary embodiment displays accordingly on a display section 5. The configuration and position for providing the display section 5 are not particularly limited. However, it is preferable to provide the display section 5 at a position that is visible to a user when driving the vehicle 1.

As illustrated in FIG. 2, the microcomputer 20, which is an example of a semiconductor device, includes a central processing unit (CPU) 40, read only memory (ROM) 42, random access memory (RAM) 44, an interface (IF) 46, and a storage section 48. The ROM 42 is stored with a chatter suppression processing program, described in detail later. The CPU 40 executes the program stored in the ROM 42 so as to function as an example of an abnormality detection section, a position detection section, and a moving body controller. The RAM 44 is employed as working memory or the like during execution of the program by the CPU 40. The IF 46 enables various information to be exchanged between the microcomputer 20 and the vibration detection sensors 22, the position detection sensors 24, and the pressing sections 26. The storage section 48 stores an abnormality occurrence position where chattering has occurred, which is an example of an abnormality occurrence position, as well as storing pressing force and the like. Specific examples of the storage section 48 include memory such as flash memory. Note that the storage section 48 is preferably a non-volatile storage section.

The CPU 40, the ROM 42, the RAM 44, the IF 46, and the storage section 48 are connected together through a bus 49.

The pressing sections 26, that are an example of an adjusting section, adjusts the force with which the wipers 15 press against the window glass 2. Note that, in the present exemplary embodiment, the force with which the wipers 15 press against the window glass 2 is referred to as "pressing".

In the present exemplary embodiment, as a specific example, each pressing section 26 includes a coil spring and a motor (geared motor). The coil spring applies force in a direction to press the wiper 15 against the window glass 2. An end portion of the coil spring is coupled to the motor (geared motor), and the motor is rotated to adjust the extension/compression of the coil spring, thereby adjusting pressing of the wipers 15 against the window glass 2. Note that, as the method for adjusting the pressing of the wipers 15 against the window glass 2 by the pressing section 26 that includes the motor, a known conventional method, such as the technology described in JP-A No. S63-159161, may be employed.

The pressing sections 26 are not limited to the above configuration, as long as they have a function of adjusting the pressing of the wipers 15. Further, since changing the position of the wipers 15 (wiper blades 14) in a direction intersecting the surface of the window glass 2 changes the pressing of the wipers 15, the pressing sections 26 may adjust the position of the wipers 15 (wiper blades 14) in a direction intersecting the surface of the window glass 2.

Next, explanation follows regarding chattering suppression operation of the microcomputer 20 of the wiper system 10 in the present exemplary embodiment.

Figure 3:
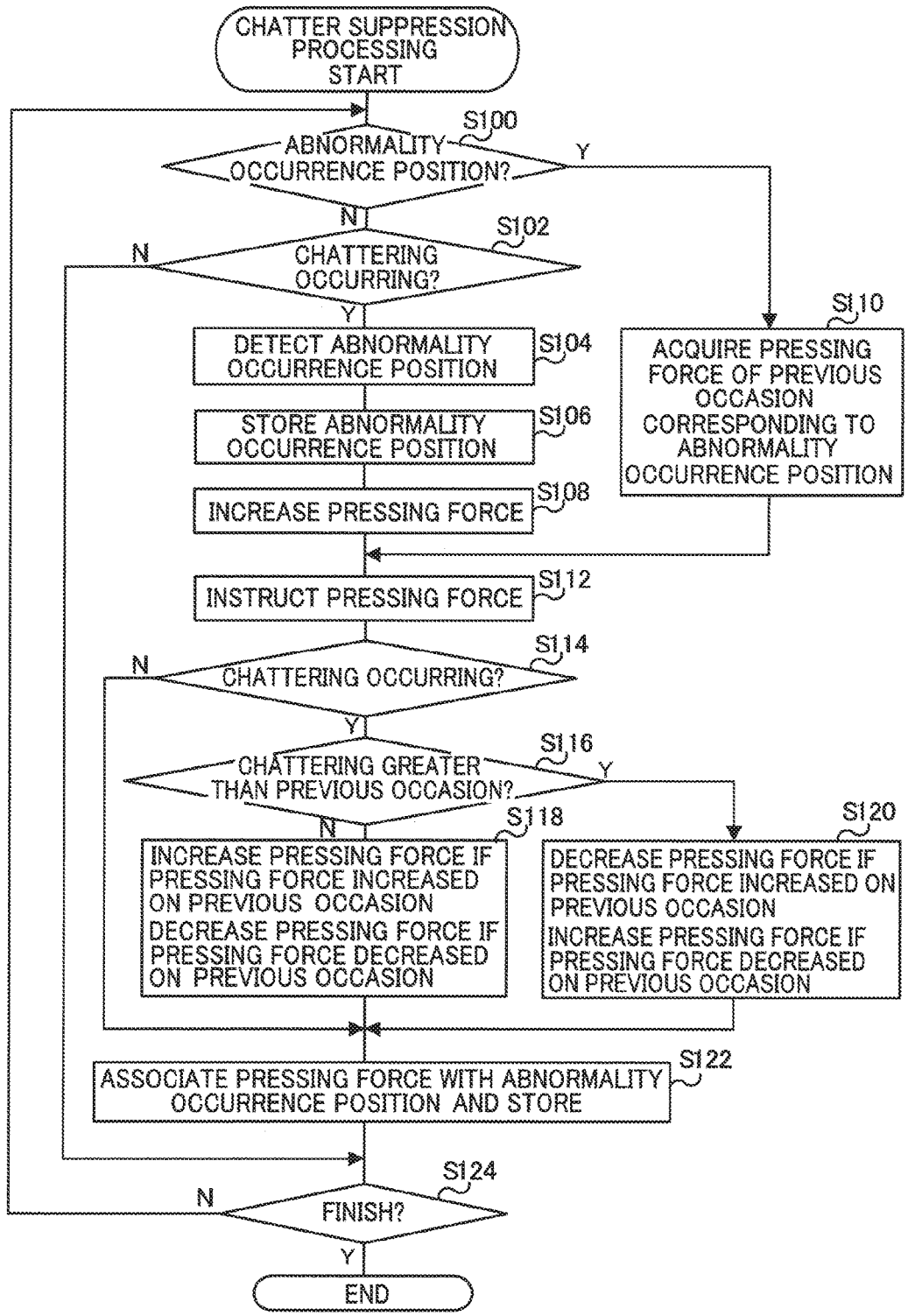
FIG. 3 is a flowchart illustrating a chatter suppression processing executed by a microcomputer of the first exemplary embodiment.

FIG. 3 is a flowchart illustrating an example of chatter suppression processing executed by the microcomputer 20. The chatter suppression processing illustrated in FIG. 3 is executed based on a signal instructing driving of the wipers 15 from the switch 3. Based on the signal input from the switch 3, the drive section 30 drives the wipers 15 using the motors 32. The chatter suppression processing illustrated in FIG. 3 is performed separately for the individual wipers 15L, 15R, and is performed at a timing that may be regarded as synchronous.

At step S100 the microcomputer 20 determines whether or not the position of each wiper 15 is at an abnormality occurrence position. In the chatter suppression processing of the present exemplary embodiment, in a case in which chattering has occurred, the position where the chattering occurred is stored in the storage section 48 at step S122, described later. Accordingly, at step S100, the microcomputer 20 determines whether or not a current position of the wiper 15, detected based on a detection result of the position detection sensor 24, matches the abnormality occurrence position stored in the storage section 48.

In a case in which there is no match, processing proceeds to step S102. At step S102, the microcomputer 20 determines whether or not chattering of the wiper 15 is occurring based on a detection result (acceleration value) of the vibration detection sensor 22. The processing proceeds to step S124 in cases in which it is determined that chattering is not occurring. The processing proceeds to step S104 in cases in which it is determined that chattering is occurring.

At step S104, the microcomputer 20 detects the abnormality occurrence position based on the detection results of the position detection sensor 24. At the next step S106, the microcomputer 20 stores the abnormality occurrence position detected at step S104 in the storage section 48. Note that chattering does not necessarily occur at the same position on the outward stroke and return stroke on the path of the wipers 15. For example, in some cases, chattering occurs on the outward stroke but does not occur on the return stroke. Accordingly, the present exemplary embodiment takes into consideration whether the abnormality occurrence position (the position where chattering occurred) is on the outward stroke or the return stroke.

At the next step S108, the microcomputer 20 increases the current pressing force, and at the next step S112, the microcomputer 20 controls the pressing section 26 such that the wiper 15 presses against the window glass 2 with the increased pressing force. Increasing the pressing of the wiper 15 is known to suppress chattering in some cases. Accordingly, in a case in which chattering has occurred, the microcomputer 20 of the present exemplary embodiment initially controls the pressing section 26 so as to increase the pressing force of the wiper 15. Increase amount of the pressing force in not particularly limited, and the increase amount may be obtained through prior testing or the like. The increase amount may also be set according to the movement speed of the wiper 15 or the like.

The pressing section 26 increases the pressing of the wipers 15 based on an instruction input from the microcomputer 20.

At the next step S114, the microcomputer 20 determines whether or not chattering of the wiper 15 is occurring, based on a detection result of the vibration detection sensor 22. In some cases, chattering may be suppressed by changing the pressing force in the processing of step S112 above, and the microcomputer 20 determines that chattering is not occurring. The processing proceeds to step S122 in cases in which it is determined that chattering is not occurring. However, the processing proceeds to step S116 in cases in which it is determined that chattering is occurring.

At step S116, the microcomputer 20 determines whether or not the chattering that occurred is greater than the chattering that occurred on the previous occasion. Specifically, the microcomputer 20 compares the acceleration value of the detection result of the vibration detection sensor 22 when it is determined that the chattering have occurred at step S102 (the previous acceleration value), with the acceleration value of the detection result of the vibration detection sensor 22 when it is determined that the chattering have occurred at step S114 (the current acceleration value). Accordingly, the microcomputer 20 determines that the chattering is greater than the previous occasion if the current acceleration value is larger.

The processing proceeds to step S120 in a case in which the chattering is determined to be greater than on the previous occasion. At step S120, the microcomputer 20 changes the pressing force. The microcomputer 20 decreases the pressing force in cases in which the pressing force has been increased compared to the previous occasion. The microcomputer 20 increases the pressing force in cases in which the pressing force has been decreased compared to the previous occasion. For example, the pressing force is decreased in cases in which the pressing force was increased at step S108. Decrease amount of the pressing force is not particularly limited, and the decrease amount obtained through prior testing or the like. The decrease amount may also be set according to the movement speed of the wiper 15 or the like. In a case in which the pressing force is adjusted by the microcomputer 20, it is preferred that the increase amount and the decrease amount for a single adjustment of the pressing force are different to each other.

The processing proceeds to step S118 in cases in which it is determined at step S116 that chattering has decreased or is unchanged compared to the previous occasion. At step S118, the microcomputer 20 changes the pressing force. The microcomputer 20 increases the pressing force in cases in which the pressing force has been increased compared to the previous occasion. The microcomputer 20 decreases the pressing force in cases in which the pressing force has been decreased compared to the previous occasion. For example, the pressing force is increased in cases in which the pressing force was increased at step S108.

The processing of steps S114 to S120 may be repeated. For example, the processing may be repeated until determination is made that chattering is not occurring at step S114. However, since the wiper 15 is moving, while repeating the processing of steps S114 to S120 the wiper 15 could move to a position where chattering would not occur anyway, even without adjusting the pressing force with the pressing section 26. Accordingly, an upper limit to the number of repetitions may be set according to the movement speed of the wiper 15 in cases in which the processing of steps S114 to S120 is repeated.

At the next step S122, the microcomputer 20 associates the current pressing force with the abnormality occurrence position and stores it in the storage section 48.

If plural abnormality occurrence positions are present along the path of the to-and-fro movement of the wiper 15, the microcomputer 20 uses the pressing section 26 to adjust the pressing for each abnormality occurrence position, and stores the pressing force each time so as to be associated with the abnormality occurrence position in the storage section 48.

At the next step S124, the microcomputer 20 determines whether or not to end the chatter suppression processing. The processing returns to step S100 in cases in which the chatter suppression processing is not ended.

In a case in which the pressing force has been associated with the abnormality occurrence position and are stored in the storage section 48 in the processing of step S122, in a case in which the wiper 15 reaches the abnormality occurrence position again as it moves to-and-fro, the microcomputer 20 determines that the position of the wiper 15 is the abnormality occurrence position by repeating execution of step S100, and the processing proceeds to step S110.

At step S110, the microcomputer 20 acquires the pressing force of the previous occasion corresponding to the abnormality occurrence position from the storage section 48, and the processing proceeds to step S112. At step S112, the microcomputer 20 controls the pressing section 26 so as to press the wiper 15 against the window glass 2 with the pressing force of the previous occasion, after which processing proceeds to step S114 and the chatter suppression processing described above is repeated.

At step S124, the microcomputer 20 determines to end processing in, for example, cases in which the user has given an instruction to stop driving the wipers 15 using the switch 3, or cases in which the engine of the vehicle 1 has stopped. The chatter suppression processing is then ended.

The wiper system 10 of the present exemplary embodiment includes the microcomputer 20, the vibration detection sensors 22, and the pressing sections 26. The microcomputer 20 determines whether or not chattering is occurring based on the detection results of the vibration detection sensors 22. The microcomputer 20 also detects the positions of the wipers 15 where abnormalities (chattering) occur based on the detection results of the position detection sensors 24. In a case in which chattering occurs, the microcomputer 20 adjusts the strength of the pressing force pressing the respective wipers 15 against the window glass 2, and controls the pressing sections 26 so as to press the window glass 2 with a pressing force at which chattering does not occur.

The microcomputer 20 of the wiper system 10 of the present exemplary embodiment detects abnormality occurrence positions using the position detection sensors 24, and associates each abnormality occurrence position with the pressing force and stores it in the storage section 48. In a case in which the wipers 15 reach the stored abnormality occurrence positions as they move to-and-fro, the microcomputer 20 controls the pressing sections 26 such that the wipers 15 press the window glass 2 with the associated pressing force.

In this manner, the microcomputer 20 of the wiper system 10 of the present exemplary embodiment controls the pressing sections 26 at the abnormality occurrence positions where chattering occur, and adjusts the pressing force according to the degree of chattering that occur at the abnormality occurrence position.

The microcomputer 20 of the wiper system 10 of the present exemplary embodiment accordingly enables appropriate control of chattering that occurs during movement of the wipers 15.

In a case in which the respective wipers 15 are at positions that are not abnormality occurrence positions (other positions), the microcomputer 20 of the wiper system 10 of the present exemplary embodiment does not control the pressing sections 26, and the pressing sections 26 are not driven. As a specific example, the pressing sections 26 of the present exemplary embodiment employ motors (geared motors) as described above. The power supply to the motors may be shut off at the other positions. This thereby enables power consumption to be suppressed in comparison to cases in which the pressing force is constantly adjusted by the pressing sections 26 while the wipers 15 are moving. Accordingly, in such case, the present exemplary embodiment may improve the electrical efficiency of the vehicle 1.

The abnormality occurrence positions change depending on the state of the window glass 2, the amount of rain, deterioration of the wiper blades 14, and the like. For example, in some cases, chattering stops occurring at a position that was previously an abnormality occurrence position. Accordingly, it is preferred to reset the abnormality occurrence positions stored in the storage section 48, and to re-detect and re-store the abnormality occurrence positions in the storage section 48. It goes without saying that the abnormality occurrence positions stored in the storage section 48 are reset when the wiper blades 14 are replaced.

Second Exemplary Embodiment

A wiper system 10 of the present exemplary embodiment may suppress power consumption and may improve electrical efficiency by transitioning to a sleep mode except for when the pressing sections 26 adjust the pressing force of the wipers 15 (at the abnormality occurrence positions).

Figure 4:
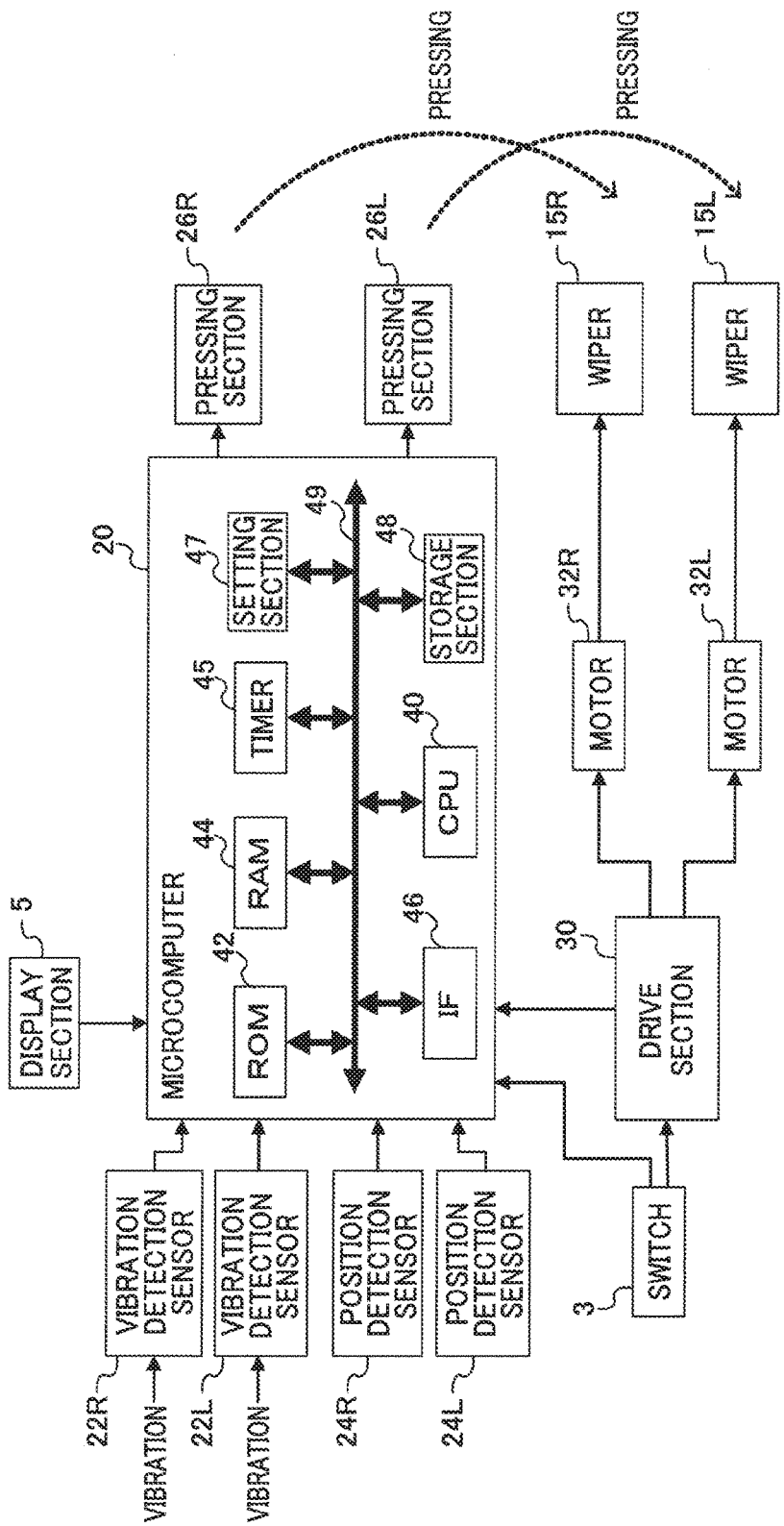
FIG. 4 is a block diagram illustrating a wiper system of a second exemplary embodiment.

First, explanation follows regarding configuration of the wiper system 10 of the present exemplary embodiment. FIG. 4 is a block diagram of a wiper system 10 of the present exemplary embodiment. As illustrated in FIG. 4, the wiper system 10 of the present exemplary embodiment differs from the wiper system 10 of the first exemplary embodiment (see FIG. 2) in the point that the microcomputer 20 includes a timer 45 and a setting section 47. Other configurations of the wiper system 10 are similar to those of the first exemplary embodiment (see FIG. 2), and therefore, detailed explanation thereof is omitted.

The microcomputer 20 of the present exemplary embodiment functions as an example of a power controller. The setting section 47 sets a timing for recovering the microcomputer 20 (CPU 40) from a sleep mode. The timer 45 measures the recover timing of the microcomputer 20 (CPU 40).

Next, explanation follows regarding chattering suppression operation of the microcomputer 20 of the wiper system 10 of the present exemplary embodiment.

In the chattering suppression of the present exemplary embodiment, the microcomputer 20 performs setting processing in which first, an abnormality occurrence position where chattering occurs is detected and stored in the storage section 48, and then a timing to recover from sleep mode is set in the setting section 47 based on the abnormality occurrence position.

Figure 5:
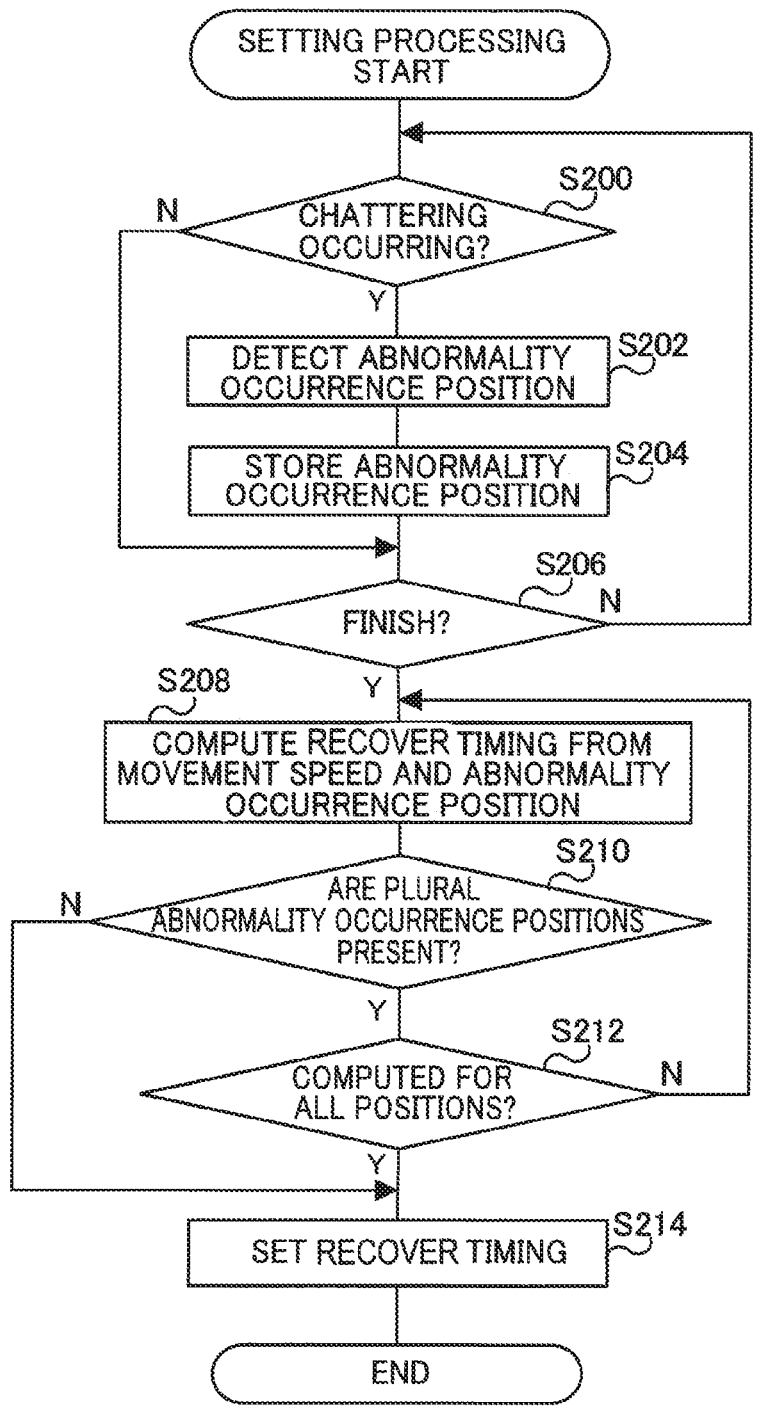
FIG. 5 is a flowchart illustrating a setting processing executed by a microcomputer of the second exemplary embodiment.

FIG. 5 is a flowchart illustrating an example of the setting processing executed by the microcomputer 20. The setting processing illustrated in FIG. 5 is executed upon input of a signal instructing driving of the wipers 15 from the switch 3. The drive section 30 drives the wipers 15 with the motors 32 based on the signal input from the switch 3. The setting processing illustrated in FIG. 5 is performed separately for the individual wipers 15L, 15R, and is performed at a timing that may be regarded as synchronous.

The respective steps S200 to S204 correspond to the respective steps S102 to S106 of the chatter suppression processing of the first exemplary embodiment (see FIG. 3).

At step S200, the microcomputer 20 determines whether or not chattering is occurring in each wiper 15, based on the detection results of the respective vibration detection sensors 22. The processing proceeds to step S206 in cases in which it is determined that chattering is not occurring. However, processing proceeds to step S202 in cases in which it is determined that chattering is occurring.

At step S202, the microcomputer 20 detects the abnormality occurrence position based on the detection result of the position detection sensor 24. At the next step S204, the microcomputer 20 stores the abnormality occurrence position detected at step S202 in the storage section 48.

At the next step S206, the microcomputer 20 determines whether or not all abnormality occurrence position detection has been completed for the entire path (outward stroke and return stroke) of the wiper 15. In a case in which this has not been completed, processing returns to step S200, and the processing of steps S200 to S204 is repeated. Note that the abnormality occurrence position detection is preferably performed by detecting over several to-and-fro movements of the wiper 15, rather than a single to-and-fro movement of the wiper 15, thereby enabling improved detection precision.

The processing proceeds to step S208 in a case in which all abnormality occurrence position detection has been completed. At step S208, the microcomputer 20 computes a recover timing for recovering from sleep mode, based on the movement speed of the wiper 15 and the abnormality occurrence position. Note that computation of the recover timing takes into consideration the time required to adjust the pressing force of the wiper 15 after recovering from sleep mode.

At the next step S210, the microcomputer 20 determines whether or not plural abnormality occurrence positions are stored in the storage section 48. The processing proceeds to step S214 if not plural (if only one abnormality occurrence position is stored). The processing proceeds to step S212 if plural abnormality occurrence positions are stored in the storage section 48.

At step S212, the microcomputer 20 determines whether or not a recover timing has been computed for all of the abnormality occurrence positions stored in the storage section 48. The processing returns to step S208 if an abnormality occurrence position is present for which a recover timing has not yet been computed, and the recover timing computation is repeated. The processing proceeds to step S214 if a recover timing has been computed for all of the abnormality occurrence positions.

At step S214, the microcomputer 20 sets the recover timings in the setting section 47, and ends the setting processing.

In a case in which the setting processing is ended in this manner, the microcomputer 20 proceeds to the sleep mode. In the present exemplary embodiment, in the sleep mode, only the timer 45 and the setting section 47 of the microcomputer 20 are active, and the supply of drive power to the other sections, including the CPU 40, is shut OFF, thereby attaining a sleeping (inactive) state. Moreover, in the present exemplary embodiment, in the sleep mode, drive of the pressing sections 26, and in particular of the motor (geared motor) of the pressing section 26, is inactivated similarly to as described above in the first exemplary embodiment. The portions for which the supply of drive power is shut OFF and that are inactive in the sleep mode are not particularly limited. However, from the perspective of suppressing power consumption, it is most preferable to inactivate the pressing section 26, and also preferable to inactivate the CPU 40. The vibration detection sensor 22 and the position detection sensor 24 may also be inactivated in addition.

The wipers 15 are driven by the drive section 30 and move to-and-fro across the window glass 2 even when the microcomputer 20 and the like are in the sleep mode.

On reaching the timing to recover from the sleep mode based on the count of the timer 45, the setting section 47 outputs an activation signal to activate the CPU 40 of the microcomputer 20. In a case in which the CPU 40 has been activated based on the activation signal, the CPU 40 generates and outputs a signal to activate the pressing section 26 and the like. When recovering from the sleep mode in this manner, the setting section 47 initially activates the CPU 40, and the CPU 40 activates the other inactive sections.

Figure 6:
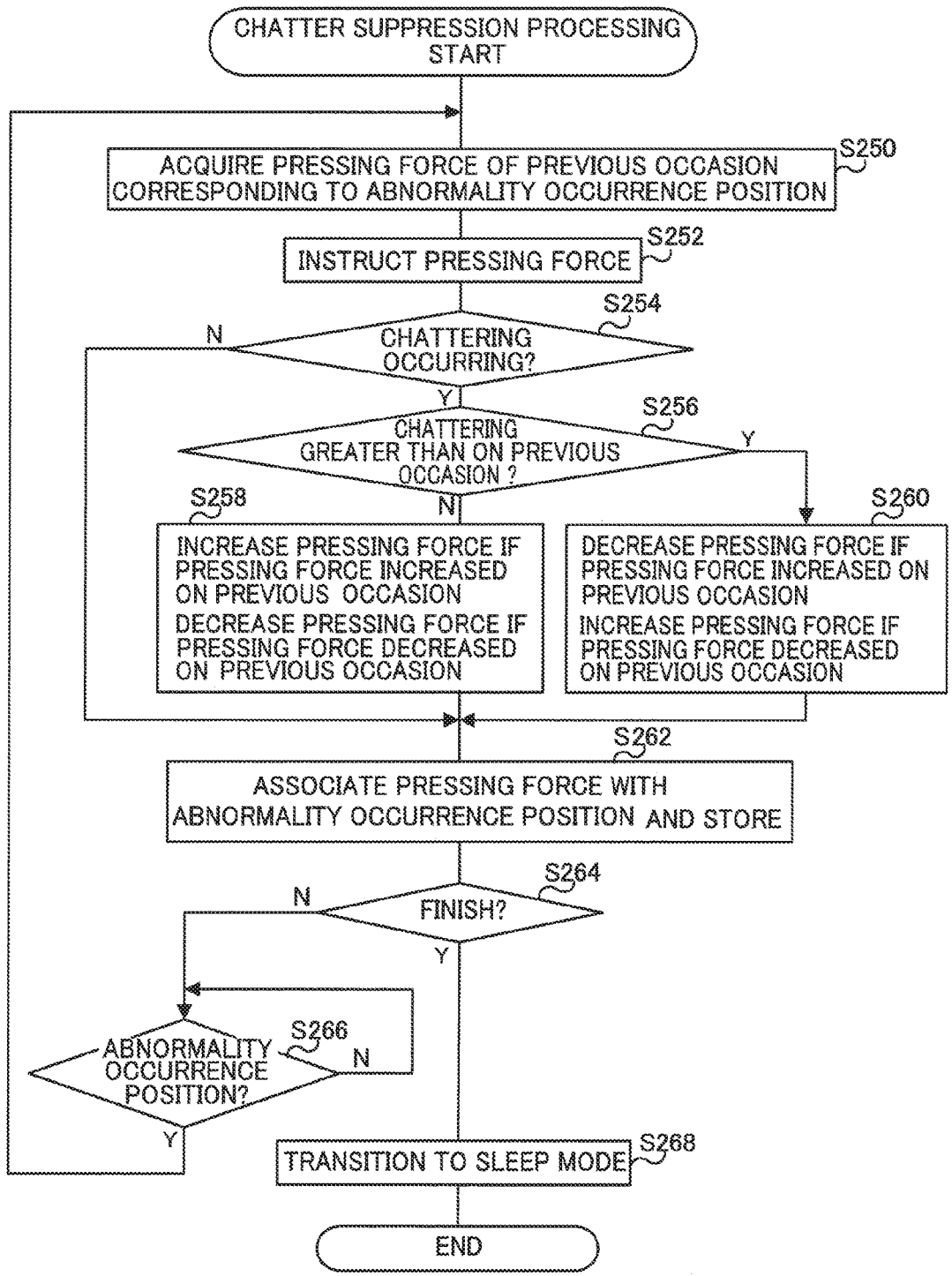
FIG. 6 is a flowchart illustrating a chatter suppression processing executed by a microcomputer of the second exemplary embodiment.

When the CPU 40 has recovered from the sleep mode, the microcomputer 20 executes the chatter suppression processing illustrated in FIG. 6. FIG. 6 is a flowchart illustrating an example of the chatter suppression processing executed by the microcomputer 20 of the present exemplary embodiment.

The respective steps S250 to S262 correspond to the respective steps S110 to S122 of the chatter suppression processing of the first exemplary embodiment (see FIG. 3).

At step S250, the microcomputer 20 acquires the pressing force corresponding to the abnormality occurrence position in the previous occasion from the storage section 48. When the wiper 15 reaches the abnormality occurrence position, the microcomputer 20 recovers from the sleep mode and acquires the pressing force of the previous occasion corresponding to the abnormality occurrence position from the storage section 48.

At the next step S252, the microcomputer 20 controls the pressing section 26 so as to press the wiper 15 against the window glass 2 with the acquired pressing force of the previous occasion. Then, the processing proceeds to step S254. At step S254, the microcomputer 20 determines whether or not chattering of the wiper 15 is occurring based on the detection results of the vibration detection sensor 22, and processing proceeds to step S262 in cases in which it is determined that chattering is not occurring. However, processing proceeds to step S256 in cases in which it is determined that chattering is occurring.

At step S256, the microcomputer 20 determines whether or not the chattering that occurred is greater than the chattering that occurred on the previous occasion, and processing proceeds to step S260 in cases in which it is determined that the chattering is greater than on the previous occasion. At step S260, the microcomputer 20 decreases the pressing force in cases in which the pressing force has been increased compared to the previous occasion, and increases the pressing force in cases in which the pressing force has been decreased compared to the previous occasion, similarly to at step S120 of the chatter suppression processing of the first exemplary embodiment (see FIG. 3).

The processing proceeds to step S258 in cases in which it is determined at step S256 that chattering has decreased or is unchanged compared to the previous occasion. At step S258, the microcomputer 20 increases the pressing force in cases in which the pressing force has been increased compared to the previous occasion, and decreases the pressing force in cases in which the pressing force has been decreased compared to the previous occasion, similarly to at step S118 of the chatter suppression processing of the first exemplary embodiment (see FIG. 3).

Note that the processing of steps S254 to S260 may be repeated, similarly to in the chatter suppression processing of the first exemplary embodiment (see FIG. 3).

At the next step S262, the microcomputer 20 associates the current pressing force with the abnormality occurrence position, and stores it in the storage section 48.

At the next step S264, the microcomputer 20 determines whether or not to end the chatter suppression processing. In cases in which there are plural of the abnormality occurrence positions, and the distance between adjacent abnormality occurrence positions is equal to or below a specific distance, after ending the chatter suppression processing for one abnormality occurrence position, the microcomputer 20 of the present exemplary embodiment goes on to perform chatter suppression processing for the adjacent abnormality occurrence position, without transitioning to the sleep mode. For example, in cases in which the distance between adjacent abnormality occurrence positions is short, the wiper 15 may reach the adjacent abnormality occurrence position before ending the activation of the CPU 40, the pressing sections 26, and the like and recovering from the sleep mode. Moreover, in some cases, it is not desirable to repeatedly transition to and recover from the sleep mode too frequently. Accordingly, in the microcomputer 20 of the present exemplary embodiment, whether or not to transition to the sleep mode is decided and set in advance, according to the distance between adjacent abnormality occurrence positions and the movement speed of the wiper 15. This setting may be performed during the above setting processing and set in the setting section 47, or may be performed separately to the above setting processing. Specific distances between adjacent abnormality occurrence positions may be obtained through advance testing or the like.

The processing proceeds to step S266 in cases in which the microcomputer 20 makes determination not to end the chatter suppression processing. At step S266, the microcomputer 20 determines whether or not the position of the wiper 15 is the abnormality occurrence position, similarly to at step S100 of the chatter suppression processing of the first exemplary embodiment (see FIG. 3). In cases in which the wiper 15 has not yet moved to an abnormality occurrence position, a standby state is entered, and in cases in which the wiper 15 has moved to an abnormality occurrence position, processing returns to step S250, and the chatter suppression processing is repeated.

The processing proceeds to step S268 in cases in which the microcomputer 20 makes determination to end the chatter suppression processing at step S264. At step S268, the microcomputer 20 shuts OFF the supply of drive power to the CPU 40, the pressing section 26, and the like, and proceeds to the sleep mode, thereby ending the present chatter suppression processing.

The chatter suppression processing is executed according to the settings of the setting section 47 as the wiper 15 moves. Namely, in a case in which the wiper 15 reaches an abnormality occurrence position, (with the exception of in cases in which the distance between adjacent abnormality occurrence positions is short, as described above) the CPU 40 of the microcomputer 20 executes the chatter suppression processing, and in a case in which the wiper 15 is at another position, the CPU 40, the pressing section 26, and the like transition to the sleep mode and become inactive.

Accordingly, in the wiper system 10 of the present exemplary embodiment, in a case in which the wiper 15 is at another position other than an abnormality occurrence position, the supply of drive power to the CPU 40, and pressing section 26, and the like is shut OFF and transitions to sleep mode. Accordingly, the present exemplary embodiment may suppress the power consumption in the wiper system 10, and may further suppress the electrical efficiency of the vehicle 1.

The abnormality occurrence positions change depending on the state of the window glass 2, the amount of rain, deterioration of the wiper blades 14, and the like. Therefore, it is preferable for the setting processing to be performed when appropriate, rather than only at an initial timing when the drive section 30 starts driving the wiper 15. Since deterioration of the wiper blades 14 has an effect on the occurrence of chattering, timings for performing the setting processing may be set based on cumulative values of the number of to-and-fro movements, the movement duration, or the like of the wipers 15, from the first use of new wiper blades 14 (since replacement), such that the setting processing is performed more frequently the greater the cumulative values becomes. Note that the timings for performing the setting processing may be set in the setting section 47, or may be set in the storage section 48 or the like.

In the setting processing, the pressing force of the wiper 15 may be adjusted so as to suppress the occurrence of chattering at the abnormality occurrence position, and the adjusted pressing force may be stored in the storage section 48 associated with the abnormality occurrence position.

The timer 45 and the setting section 47 may be provided externally to the microcomputer 20.

As described above, the microcomputer 20 of the wiper system 10 of the respective exemplary embodiments described above detects the occurrence of chattering of the wiper 15 moving along a specific path over the surface of the window glass 2, and detects the position of the wiper 15 where the occurrence of chattering was detected as an abnormality occurrence position, and stores the abnormality occurrence position in the storage section 48. Moreover, the microcomputer 20 controls the pressing section 26 so as to adjust the pressing force with which the wipers 15 press against the window glass 2, based on the abnormality occurrence position information and the detection results of the vibration detection sensors 22. Alternatively, the microcomputer 20 controls the pressing sections 26 so as to adjust the positions of the wipers 15 in a direction intersecting the surface of the window glass 2 based on the abnormality occurrence position information and the detection results of the vibration detection sensors 22.

Accordingly, the microcomputer 20 of the wiper system 10 of the present exemplary embodiment controls the pressing sections 26 at each abnormality occurrence position where chattering has occurred, adjusting the pressing force according to the amount of chattering that occurred at that abnormality occurrence position.

Accordingly, the microcomputer 20 of the wiper system 10 of the present exemplary embodiment may appropriately control chattering that occurs during movement of the wipers 15.

Further, since chattering may be appropriately controlled, the wiper system 10 of the present exemplary embodiment may suppress the annoyance caused to the user, for example the driver, due to chattering, even in a case in which the wiper blades 14 cannot be replaced immediately. Moreover, since chattering may be appropriately controlled, the wiper system 10 of the present exemplary embodiment may appropriately remove the water droplets that have adhered on the window glass 2, and may maintain a good field of vision for the user, for example, the driver.

Preferably, a maximum value and a minimum value of the pressing force that is adjusted by the microcomputer 20 are predetermined. For example, if the pressing force is too large, there could be a concern of the wipers 15 pressing the window glass 2 too hard and damaging the window glass 2 and/or the wipers 15. Conversely, for example, if the pressing force is too small, there could be a concern of the wipers 15 lifting off the window glass 2 and failing to wipe the window glass 2. Accordingly, it is preferable to predetermine the maximum value and the minimum value of the pressing force that is adjusted by the microcomputer 20. Further, it is preferable so that the microcomputer 20 controls the pressing sections 26 such that the wipers 15 press against the window glass 2 with the pressing force that gives the minimum amount of vibration, in cases in which chattering still occurs even at the maximum value or the minimum value. In such cases, since there is a concern that the wiper blades 14 may have deteriorated. Accordingly, a display indicating that chattering cannot be suppressed from occurring may be made using the display section 5. Such a display can prompt the user to inspect or replace the wiper blades 14.

Moreover, there is a concern that, for example, the wiper blades 14 may have deteriorated in cases in which plural abnormality occurrence positions are present. In such cases, the microcomputer 20 may use the display section 5 to make a display prompting the user to inspect or replace the wiper blades 14, according to the number of abnormality occurrence positions.

Note that such displays to prompt the user to inspect or replace the wiper blades 14 are preferable to be performed after turning OFF the engine of the vehicle 1, and when the engine is restarted.

In the respective exemplary embodiments described above, explanation has been given regarding cases in which the vibration detection sensors 22 are provided to the wiper arms 12. However, the positions where the vibration detection sensors 22 are provided are not limited thereto. For example, the vibration detection sensors 22 may be provided to the wiper blades 14. The positions for providing the vibration detection sensors 22 to the wiper arms 12 or the wiper blades 14 (end portions, central portions, or the like) are likewise not particularly limited. The vibration detection sensors 22 may also be provided to the window glass 2 instead of the wipers 15. Providing the vibration detection sensors 22 to the window glass 2 may enable a simpler wiring layout than in a case in which the vibration detection sensors 22 are provided to the wipers 15, and also may improve durability since the effects due to the movement of the wipers 15 to the vibration detection sensors 22 can be suppressed. Similarly to the vibration detection sensors 22, the positions for providing the position detection sensors 24 are obviously likewise not limited to those in the respective exemplary embodiments described above.

The respective detection results output from the vibration detection sensors 22 and the position detection sensors 24 may be output to the microcomputer 20 through wires, or may be output to the microcomputer 20 wirelessly. Note that employing a wireless communication enables the number of wires to be suppressed.

Drive of the vibration detection sensors 22, the position detection sensors 24, and the like may employ power supplied from a power source supply section (not illustrated in the drawings) provided to the vehicle 1, may employ energy harvesting (environmental power generation), or may employ power generated utilizing the vibrations arising due to chattering. In such cases, a power supply section may be provided to convert vibrations arising due to chattering into power, and supply the power to the vibration detection sensors 22, the position detection sensors 24, and the like. Note that the power supplied from the power supply section is not limited to use in at least one of the vibration detection sensors 22 or the position detection sensors 24, and may be used to drive both types of sensor, as well as being used to drive the microcomputer 20, the wiper system 10, or the like.

The position of the window glass 2 on the vehicle 1, the number and placement of the wipers 15, and the like are not limited to those in the respective exemplary embodiments described above. Moreover, the type of the vehicle 1 is not particularly limited, and may be an automobile, a train, an aircraft, or the like.

The wipers 15 are an example of a moving body of the present disclosure. However, the moving body is not particularly limited as long it is a moving body that moves along a specific path across a surface of a specific object. For example, the moving body may be a cleaning blade that wipes the surface of a photosensitive body of an image forming device.

Other configurations and operation of the wiper system 10 and the microcomputer 20 explained in the respective exemplary embodiments described above are merely examples thereof, and obviously modifications are possible according to the circumstances, within a range not departing from the spirit of the present disclosure.

What is claimed is:

1. A moving body control device configured to control a moving body that moves along a specific path on a surface of a specific object, the moving body control device comprising:
 a storage section; and
 a microcomputer connected to the storage section, the microcomputer being configured to
 detect an abnormality occurring in the moving body moving along the specific path;
 detect a position of the moving body as an abnormality occurrence position, in a case in which an abnormality has been detected;
 store, in the storage section, abnormality occurrence position information expressing the abnormality occurrence position; and
 control an adjusting section to adjust a pressing force at which the moving body presses against the surface of the specific object, based on the abnormality occurrence position information,
 wherein the adjusting section adjusts the pressing force of the moving body at the abnormality occurrence position by increasing or decreasing the pressing force,
 wherein the microcomputer is further configured to
 in a case in which the pressing force has been increased,
 determine whether the abnormality occurring in the moving body has increased or decreased compared to the abnormality before the pressing force was increased; and
 control the adjusting section to decrease the pressing force in a case in which the microcomputer determines that the abnormality has increased, and to increase the pressing force in a case in which the microcomputer determines that the abnormality has decreased, or
 in a case in which the pressing force has been decreased,
 determine whether the abnormality occurring in the moving body has increased or decreased compared to the abnormality before the pressing force was decreased; and
 control the adjusting section to increase the pressing force in a case in which the microcomputer determines that the abnormality has increased, and to decrease the pressing force in a case in which the microcomputer determines that the abnormality has decreased, and
 wherein the specific object is a vehicle window, the moving body is a wiper, and the abnormality is chattering.

2. The moving body control device of claim 1, wherein the microcomputer is further configured to:
 determine whether the abnormality occurring in the moving body has increased or decreased in a case in which the pressing force of the moving body at the abnormality occurrence position has been adjusted; and
 control the adjusting section to re-adjust the pressing force of the moving body based on a determination of whether the abnormality occurring in the moving body has increased or decreased.

3. The moving body control device of claim 1, wherein the microcomputer is further configured to store the adjusted pressing force in association with the abnormality occurrence position, in a case in which the pressing force of the moving body at the abnormality occurrence position has been adjusted.

4. The moving body control device of claim 1, further comprising a power controller that controls at least one of drive power supplied to the adjusting section from a power source, or the drive power supplied to the moving body control device from the power source, based on the abnormality occurrence position information.

5. The moving body control device of claim 4, wherein, based on the abnormality occurrence position information, the power controller causes the drive power to be supplied to the moving body control device in a case in which the moving body is within a specific range from the abnormality occurrence position, and causes the drive power not to be supplied to at least one of the adjusting section or the moving body control device in a case in which the moving body is at any position outside the specific range.

6. The moving body control device of claim 5, wherein, in a case in which a plurality of abnormality occurrence positions have been detected, the power controller causes the drive power to be supplied to the adjusting section and to the moving body control device even in a case in which the moving body is at the any position outside the specific range, based on at least one of a number of the plurality of the abnormality occurrence positions, a distance between adjacent abnormality occurrence positions from among the plurality of the abnormality occurrence positions, or a movement speed of the moving body.

7. The moving body control device of claim 1, further comprising:
 an abnormality detection sensor that detects the abnormality; and
 a position detection sensor that detects the position of the moving body.

8. A wiper system, comprising:
 the wiper;
 a wiper drive section that moves the wiper to-and-fro across the surface of a vehicle window; and
 the moving body control device of claim 1.

* * * * *